United States Patent
Brun et al.

(10) Patent No.: US 6,358,469 B1
(45) Date of Patent: Mar. 19, 2002

(54) ODOR ELIMINATING AQUEOUS FORMULATION

(75) Inventors: Anne M. Brun; Wayne M. Rees, both of Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/204,104

(22) Filed: Dec. 1, 1998

(51) Int. Cl.⁷ .................................................. A61L 9/01
(52) U.S. Cl. ........................ 422/5; 424/76.1; 424/76.21; 424/76.5; 424/641
(58) Field of Search ........................ 422/4, 5; 424/76.1, 424/76.5, 76.21, 641

(56) References Cited

U.S. PATENT DOCUMENTS

| | | |
|---|---|---|
| 2,544,093 A | 3/1951 | Kilgore |
| 3,074,891 A | 1/1963 | Kulka |
| 3,159,535 A | 12/1964 | Sesso et al. |
| 3,172,817 A | 3/1965 | Leupold et al. |
| 3,426,011 A | 2/1969 | Parmerter et al. |
| 3,453,257 A | 7/1969 | Parmerter et al. |
| 3,453,258 A | 7/1969 | Parmerter et al. |
| 3,453,259 A | 7/1969 | Parmerter et al. |
| 3,453,260 A | 7/1969 | Parmerter et al. |
| 3,459,731 A | 8/1969 | Gramera et al. |
| 3,553,191 A | 1/1971 | Parmerter et al. |
| 3,565,887 A | 2/1971 | Parmerter et al. |
| 3,974,270 A | 8/1976 | Kenkare et al. |
| 4,138,477 A | 2/1979 | Gaffar |
| 4,265,899 A | 5/1981 | Lewis et al. |
| 4,325,939 A | 4/1982 | Shah |
| 4,449,987 A | 5/1984 | Lindauer |
| 4,469,674 A | 9/1984 | Shah et al. |
| 4,535,152 A | 8/1985 | Szejtli et al. |
| 4,616,008 A | 10/1986 | Hirai et al. |
| 4,638,058 A | 1/1987 | Brandt et al. |
| 4,678,598 A | 7/1987 | Ogino et al. |
| 4,693,890 A | 9/1987 | Wilson et al. |
| 4,696,676 A | 9/1987 | Wilson et al. |
| 4,727,824 A | 3/1988 | Ducharme et al. |
| 4,746,734 A | 5/1988 | Tsuchiyama et al. |
| 4,818,524 A | 4/1989 | Gibbs |
| 4,840,792 A | 6/1989 | Joulain et al. |
| 4,902,434 A | * 2/1990 | Dickerson |
| 4,909,986 A | 3/1990 | Kobayashi et al. |
| 4,933,371 A | 6/1990 | Hink et al. |
| 4,938,416 A | 7/1990 | Bertrand et al. |
| 4,946,672 A | 8/1990 | Gibbs |
| 4,963,287 A | 10/1990 | Hutchings et al. |
| 4,983,578 A | 1/1991 | Cashman et al. |
| 5,076,960 A | 12/1991 | Hutchings et al. |
| 5,089,258 A | 2/1992 | Zaid |
| 5,102,564 A | 4/1992 | Gardlik et al. |
| 5,196,200 A | 3/1993 | Wilson et al. |
| 5,211,870 A | 5/1993 | Gilbert et al. |
| 5,234,610 A | 8/1993 | Gardlik et al. |
| 5,234,611 A | 8/1993 | Trinh et al. |
| 5,490,982 A | 2/1996 | Siciliano |
| 5,578,563 A | 11/1996 | Trinh et al. |
| 5,589,164 A | * 12/1996 | Cox et al. ................... 424/76.5 |
| 5,593,670 A | 1/1997 | Trinh et al. |
| 5,663,134 A | 9/1997 | Trinh et al. |
| 5,668,097 A | 9/1997 | Trinh et al. |
| 5,714,137 A | 2/1998 | Trinh et al. |
| 5,783,544 A | 7/1998 | Trinh et al. |

FOREIGN PATENT DOCUMENTS

| | | |
|---|---|---|
| EP | 0032779 | 6/1983 |
| EP | 0386714 | 3/1990 |
| EP | 0401140 | 12/1990 |
| FR | 2579979 | * 10/1986 |
| GB | 941105 | 5/1962 |
| JP | 58-124452 | 7/1983 |
| JP | 61-128973 | 6/1986 |
| JP | 63-164953 | 7/1988 |
| JP | 1-256596 | 10/1989 |
| JP | 1-256597 | 10/1989 |
| JP | 2-251681 | 10/1990 |
| JP | 3-170415 | 7/1991 |
| JP | 3-284616 | 12/1991 |
| JP | 10-110187 | * 4/1998 |
| WO | 89/02698 | 4/1989 |
| WO | 91/12029 | 8/1991 |
| WO | 95/15186 | 6/1995 |
| WO | 96/04940 | 2/1996 |

OTHER PUBLICATIONS

NEODOX Alcohol Ethoxycarboxylate, Shell Chemical Company, Oct. 1994.
NEODOX Alcohol Ethoxycarboxylate (AEC) TSCA Regulatory Status, Technical Bulletin Shell Chemical Company, Mar. 1997.
NONIDET SF–5, Chemical Company, Oct. 1994.

\* cited by examiner

*Primary Examiner*—Elizabeth McKane

(57) ABSTRACT

A deodorizing composition formed by an aqueous solution of divalent metal ions, preferably zinc ions, and i) an anionic alkylaryl alkoxy carboxylate/carboxylic acid surfactant and/or ii) an anionic alcohol alkoxy carboxylate/carboxylic acid surfactant.

18 Claims, No Drawings

ODOR ELIMINATING AQUEOUS FORMULATION

BACKGROUND OF THE INVENTION

1. Field of the Invention

The present invention relates to as aqueous formulation that substantially reduces odors. In particular, the invention relates to an aqueous solution of divalent metal ions, most preferably zinc ions, and an anionic alkoxy carboxylate/carboxylic acid surfactant.

2. Related Background

Offensive odors are a common problem. For example, offensive odors can emanate from contaminant materials, decaying materials, or incompatible materials. Even when such materials have been substantially removed, offensive odors can continue to be noticeable because of the high olfactory sensitivity of people. Further, offensive odors are caused by a variety of materials in a variety of environments. Thus, different deodorizing applications have varying requirements. Accordingly, there is a continuing need for deodorizing compositions to substantially eliminate offensive odors.

Attempts to ameliorate offensive odors include the use of perfumes to mask such malodors. U.S. Pat. No. 5,490,982 describes a cosmetic microemulsion compositions that is formed by two immiscible liquid phases containing isoeicosane, water, a fragrance, and a fatty glyceride ester alkoxylated with alkylene oxide such as alkylene oxide alkoxylated caprylic/capric fatty glyceride ester. U.S. Pat. No. 4,938,416 describes a water based fragrance dispersion that includes a fragrance oil and a fragrance enhancer such as an alcohol, ester, ketone, aldehyde, acid, terpene, ether, or other complex materials. A preferable nonionic surfactant such as nonylphenol polyoxyethylene or polyoxyethylene sorbitan monooleate can be included.

Other attempts to form a composition that deodorizes include U.S. Pat. No. 5,076,960 which describes an aqueous composition containing alkali metal halogenites such as sodium chlorite, a salt of a transition or post transition metal such as zinc chloride, and an alcohol to assist in stabilizing the sodium chlorite. The composition can include a perfume, in which case the perfume can be stabilized against the alkali metal halogenite by the use of an anionic surfactant. U.S. Pat. No. 4,963,287 also describes a cleaner composition which includes an alkali metal halogenite, a perfume, and an anionic surfactant to stabilize the perfume. International Patent Publication WO 95/15186 and European Patent Publication EP 0 401 140 B1 describe deodorizing compositions containing aldehydes.

U.S. Pat. No. 4,840,792 describes a composition for neutralizing bad smells utilizing a compound that is an aliphatic alcohol, aldehyde, aliphatic ketone, aliphatic ester, aromatic lactone, phenol, aromatic ether, amine, or an aromatic amine. U.S. Pat. Nos. 4,946,672 and 4,818,524 describe deodorizing compositions containing imino (HN=) moieties such a polymeric biguanide. U.S. Pat. No. 3,172,817 describes deodorizing compositions containing a beta-diketone.

British Patent No. 941,105, and U.S. Pat. Nos. 2,544,093, and 3,074,891 describe deodorizing compositions containing esters of alpha,beta-unsaturated monocarboxylic acids. U.S. Pat. No. 5,089,258 describes deodorizing compositions containing citric acid and a monovalent salt of citric acid. U.S. Pat. No. 5,211,870 describes deodorizing compositions containing a zeolite. International Patent Publication No. WO 91/12029 describes deodorizing compositions containing zeolite and an absorbent gelling material.

U.S. Pat. No. 4,983,578 describes deodorizing compositions containing hydroxyphosphoric acid, polyalkylene glycol alkyl ether, alcohol, and perfume. U.S. Pat. No. 4,909,986 describes aqueous deodorizing compositions containing a water-soluble organic polymer having a carboxyl group and its ammonium salt. Organic monobasic acids and their salts may be included. The salts may include alkali metal salts, calcium salts, iron salts, ammonium salts and alkanol/alkanol-amine salts.

Insect repellents can present unpleasant odors. Further, repellents can be more effective if the applied surface is better coated. Accordingly, repellant compositions can contain perfumes and surfactants. U.S. Pat. Nos. 4,696,676, 4,933,371, and 5,196,200 describe repellents formed from alcohols such as 1-nonen-3-ol and linalool, while U.S. Pat. No. 4,449,987 describes a fragrant insect repellent composition that includes methyl heptenone, coumarin, and an indole. Perfumes and surfactants may be included in these insect repellant compositions.

European Patent Publication 0 386 714 describes the use of monoterpenes such as borneol, isoborneol, camphor, and isobornyl acetate as a deodorizer and insect repellant.

Deodorants can be in the form of an aerosol composition. U.S. Pat. No. 3,159,535 describes an aerosol composition that is a liquid/liquid/gas three phase composition which includes an emulsifier which can be anionic, cationic or nonionic. Particularly suitable emulsifiers include long chain fatty acid esters of polyhydrocylic compounds such as the glycol, glycerol and sorbitol esters of oleic, stearic, palmitic and lauric acids; and ethoxylated fatty acids and amides. U.S. Pat. No. 3,974,270 describes an aerosol composition using a water soluble poly-lower alkoxylated cetyl alcohol such as cetyl propoxylate as a vehicle for aluminum chlorhydrate. European Patent Publication No. 0 032 779 describes water-based aerosol compositions containing dimethylether, perfume, and an ethylene oxide/propylene oxide block copolymer surfactant.

Zinc compounds have been used in oral and dental compositions to reduce calculus formation and to inhibit offensive mouth odors. U.S. Pat. No. 4,469,674 describes a composition containing zinc salt and a soluble ionic fluoride salt. U.S. Pat. No. 4,325,939 describes a composition containing an alkali metal zinc citrate or ammonium zinc citrate.

U.S. Pat. No. 4,138,477 describes a composition, to control mouth odors, containing a combination formed from a zinc salt and an anionic polymer. The anionic polymer includes carboxyl, sulfonic or phosphonic acid groups with which the zinc ion reacts.

Many attempts to control odor utilize cyclodextrin or derivatives of cyclodextrin. U.S. Pat. Nos. 3,426,011, 3,453,257, 3,453,258, 3,553,191, 3,565,887, 4,535,152, 4,638,058, 4,616,008, 4,678,598, 4,727,824, 4,746,734, 5,102,564, 5,234,610, 5,234,611, 5,578,563, 5,593,670, 5,663,134, 5,668,097, 5,714,137, 5,783,544, Japanese Patent Nos. JP 58-124452, JP 61-128973, JP 63-164953, JP 3-170415, JP 2-251681, JP 1-256597, JP 1-256596, and JP 3-284616, and International Patent Publications WO 89/02698 and WO 96/04940 describe particular perfumes, cyclodextrins, derivatives of cyclodextrin, and various compositions containing cyclodextrins, and/or its derivatives. Additional ingredients such as metallic salts such as zinc salts, anionic polymeric soil release agents, alkali carbonates and bicarbonates, clays, and surfactants are also described. U.S. Pat. No. 5,663,134 states, however, that when metallic salts such as zinc salts are utilized, anionic surfactants are not preferred because water-insoluble salts can form.

As described above, surfactants are desirably included in deodorizing compositions used for many applications to assist in forming a complete, uniform coverage of the malodorous substrate by the applied composition. Surfactants can be described as cationic, nonionic, or anionic in accordance with their ionic properties, well known to one in the art. Anionic surfactants have a negative valence charge and are generally provided in association with a cation. When divalent cationic zinc is used in deodorizing compositions, nonionic or cationic surfactants are conventionally used in order to assure that the zinc ions remain in solution.

U.S. Pat. No. 4,902,434 describes a dry granular composition, for the neutralization of odors and the removal of soil, formed from a divalent transition metal salt coated onto a solid inorganic granular carrier effective to bound malodorous materials to the surface of the carrier which then can be removed along with the dry granular carrier. Anionic surfactants such as sodium lauryl sulfate and magnesium lauryl sulfate can be used.

Without being bound to theory, it is believed that zinc ions in solution are more readily available to react with malodorous odor molecules than are zinc ions in a solid form (as a salt). Accordingly, it would be desirable to form a deodorizing composition that contains zinc ions in aqueous solution, together with an anionic surfactant that imparts improved flow and coating properties to the solution while maintaining the zinc ions in solution, to facilitate reactions of the zinc with malodorous molecules.

SUMMARY OF THE INVENTION

The present invention is directed to a deodorizing composition comprising an aqueous solution of divalent metal ions, preferably zinc ions, and an anionic surfactant. The anionic surfactant is described by the formula $R-(O-CH_2-CH_2)_x-O-CH_2COO^-$, wherein R is a fatty alcohol substituent or an alkylaryl substituent. The fatty alcohol substituent is a residue of a $C_6-C_{20}$ fatty alcohol, the alkylaryl substituent is a residue of a $C_{10}-C_{20}$ alkylaryl compound, and X is at least 2. The metal divalent metal ions are present in a concentration that is effective to deodorize a substrate to which the solution is applied. The anionic surfactant is present in a concentration effective to maintain the metal ions in solution.

The aqueous solution of this invention advantageously may be a clear solution that can be formulated so that its application to a substrate in a deodorizing effective amount does not leave a visible residue on the substrate.

The invention is also directed to a method to deodorize a substrate, comprising the step of applying the above-described deodorizing composition.

DETAILED DESCRIPTION OF THE INVENTION

The present invention is directed to a deodorizing composition that is an aqueous solution containing divalent metal ions and an anionic surfactant. The divalent metal ions are preferably copper or zinc, and most preferably zinc ions. The anionic surfactant is described by the formula $R-(O-CH_2-CH_2)_x-O-CH_2COO^-$, wherein R is a fatty alcohol substituent or an alkylaryl substituent.

There should be at least two moles of the ethoxylate for each mole of surfactant molecule—that is, X should be at least 2. Preferably, X is from 2 to 20, most preferably, X is from 5 to 15.

When R is a fatty acid substituent, R should contain from 6 to 20 carbon atoms—that is, R should be formed from a $C_6-C_{20}$ fatty alcohol. The fatty alcohol substituent provides hydrophobic functionality to the surfactant, balancing the hydrophilic functionality of the poly(ethylene oxide) carboxylate. Surfactants containing fatty alcohol substituents having carbon numbers below 6 disadvantageously are unlikely to provide adequate film forming and surface wetting properties.

When R is an alkylaryl substituent, the alkyl portion(s) should contain from 4 to 14 carbon atoms—that is, the overall alkylaryl substituent should be a $C_{10}-C_{20}$ substituent.

The anionic surfactant described by the formula $R-(O-CH_2-CH_2)_x-O-CH_2COO^-$, wherein R is a fatty alcohol substituent, can be called an alcohol ethoxycarboxylate. The alcohol ethoxycarboxylate can be supplied associated with any convenient cation such as for example, $H^+$, $Na^+$, $K^+$, or $NH_4^+$. Any suitable convenient alcohol ethoxycarboxylic acid or alcohol ethoxycarboxylate can be used such as, for example, NEODOX™ alcohol ethoxycarboxylic acids from Shell Chemicals, Houston, Tex., and SANDOPAN® carboxylated surfactants from Clariant Corporation, Charlotte, N.C.

The anionic surfactant described by the formula $R-(O-CH_2-CH_2)_x-O-CH_2COO^-$, wherein R is an alkylaryl substituent can be called an alkylaryl ethoxycarboxylate. The alkylaryl ethoxycarboxylate can be supplied associated with any convenient cation such as for example, $H^+$, $Na^+$, $K^+$, or $NH_4^+$. Any suitable convenient alkylaryl ethoxycarboxylic acid or alkylaryl ethoxycarboxylate can be used such as, for example, SANDOPAN® MA-18 carboxylated surfactants from Clariant Corporation, Charlotte, N.C.

The preferred divalent zinc ions can be supplied by any convenient source such as, for example, zinc chloride, zinc acetate, zinc bromide, zinc acetate, zinc salicylate, zinc propionate, zinc gluconate, zinc lactate, zinc maleate, zinc sulfate or zinc nitrate.

The zinc ions should be in the amount of from about 0.01 wt % to about 5 wt % of the total aqueous deodorizing composition. Preferably, the zinc ions should be in the amount of from about 0.02 wt % to about 2 wt %, more preferably from about 0.03 wt % to about 0.3 wt %. All percentages recited herein are weight percentages unless specifically stated otherwise.

The required anionic surfactant(s) used in the inventive composition advantageously provides multiple functions: i) as an emulsifier for added fragrance ingredients, ii) as a wetting agent, iii) as a control release agent for the zinc, and iv) as a deodorizer itself. The first two properties are apparent. In regard to the third property, without being held to theory, it is believed that the control release agent properties of the surfactants of the present invention derive from the interaction of the anionic surfactant with the zinc +2 cation. It is believed that the zinc is lightly bound (weakly chelated) to the anionic surfactant. Thus, the zinc is sufficiently bound to maintain its solubility, yet sufficiently weakly bound so as to be available for reaction with malodorous molecules. It is believed that zinc reacts with the reduced sulfur compounds, such as thiols and disulfides, and amines that are often present as malodorous molecules. The zinc binds with the malodorous molecules to lower the volatility of the malodorous molecules, thus reducing and eliminating odor. Further, the anionic surfactant itself can react with malodorous molecules such as amines to reduce odor.

The pH of the aqueous composition of this invention should be acidic to about very slightly basic. Preferably, the pH should be from about 3 to about 8. More preferably, the pH should be from about 4 to about 7. Most preferably, the pH should be from about 4 to about 6. In general, a lower pH helps maintain solubilization and availability of the zinc cation.

Accordingly, another important function of the acid form of the anionic surfactants of the invention is to adjust the pH of the aqueous solution. The anionic surfactants of the invention can be used as a mixture of suitable anionic surfactants. Thus, a mixture of ethoxylated carboxylic acids and ethoxylated carboxylates can be used to conveniently adjust and control the solution pH. For example, a 1:1 mixture of SANDOPAN® DTC acid and SANDOPAN® LS-24-N have been conveniently used to control pH at about 5 or below.

The weight ratio of zinc to surfactant should be from about 1:2 to about 1:40. The anionic surfactant of the present invention should be from about 0.005 wt % to about 10 wt % of the total aqueous solution. Preferably, the anionic surfactant should be from about 0.2 wt % to about 1.0 wt %, and more preferably from about 0.50 wt % to about 0.75 wt %.

Other compatible constituents can be included in the aqueous formulations of this invention. Perfumes can be included to mask odors and to impart a pleasant fragrance to the solution. Miscible cosolvents such as, for example, isopropyl alcohol (isopropanol), ethanol, propylene glycol, or mixtures thereof can be included. Such cosolvents conveniently include, for example, glycol ethers such as R—(OCH$_2$CH$_2$)$_x$OH, wherein R is a methyl, ethyl, propyl, butyl or hexyl substituent, and x is 1 or 2, and the corresponding propylene oxide based glycol ethers represented by the formula R—(OCH(CH$_3$)CH$_2$)$_x$OH, wherein R is a methyl, ethyl, propyl, butyl or hexyl substituent, and x is 1 or 2. Such cosolvents can be included, for example, to assist in drying of the applied solution. Compatible colorants can be included to impart a pleasing color or to identify areas that have been treated with the aqueous solution. Various organic and inorganic acids may be included for pH control. Any other suitable compatible additive can be conveniently included such as, for example, preservatives, antifungal agents, and bacterial control agents.

The aqueous solution of the invention can be applied by any convenient method such as, for example, by spraying, wiping, pouring, or dipping. The application can be from any convenient applicator such as, for example, a pump spray container, an aerosol spray container, a sponge, a cloth, a synthetic composite applicator, a bottle, or a tray.

Examples

The Examples which follow are intended as an illustration of certain preferred embodiments of the invention, and no limitation of the invention is implied.

The aqueous solutions of the invention were tested against common malodors (smoke, pet smells, cooking odors, and mildew). The tests were performed over 24 hour periods. A rating was made on a scale of 1–5 where 1 represents the odor totally removed, while 5 represents the odor unchanged. Averages were calculated of the ratings after 5 minutes, 20 minutes, and 24 hours. The present invention was efficacious in all cases, exhibiting an average rating of about 2 or lower.

Examples 1–4

In Examples 1–4, SANDOPAN® LS-24-N (Clariant Corp.), a sodium laureth-13-carboxylate anionic surfactant, was warmed to 50° C. Then, SANDOPAN® DTC (Clariant Corp.), a trideceth-7-carboxylic acid anionic surfactant, was mixed in at a weight ratio of 1:2 LS-24-N:DTC to form an anionic surfactant mixture. Next, a compatible perfume was added to the anionic surfactant mixture at a weight ratio of at least 1:5 perfume:surfactant to form an anionic surfactant/perfume mixture.

Separately, water, isopropanol, and propylene glycol were mixed together with a quantity of the previously formed anionic surfactant/perfume mixture. Zinc chloride was then added to form the formulations (in wt %) shown in the table below. In these examples, the pH were approximately 4.3–4.5 and the final solutions were clear.

|  | Example | | | |
| --- | --- | --- | --- | --- |
|  | 1 | 2 | 3 | 4 |
| Zinc Chloride | 0.05 | 0.5 | 1.0 | 1.5 |
| IPA | 2.0 | 2.0 | 5.0 | 7.0 |
| Perfume | 0.15 | 0.1 | 0.15 | 0.2 |
| Total Surfactant | 0.75 | 0.5 | 0.9 | 1.5 |
| Propylene Glycol | 0.05 | 0.05 | 0.00 | 0.00 |
| Water | to Balance | | | |

Examples 5–9

In Examples 5–9, the solvents isopropyl alcohol (IPA) and propylene glycol were added to water under slow stirring. The perfume and surfactants were then added as a premixed liquid similarly as in Example 1, while stirring, until dissolved. The zinc chloride was then added. The pH was below 5 in each example. The formulations are shown in wt % (with the balance water) in the table below.

|  | Example | | | | |
| --- | --- | --- | --- | --- | --- |
|  | 5 | 6 | 7 | 8 | 9 |
| Citric Acid | 0.1 | 0.2 | 0.2 | 0.2 | 0.2 |
| Sodium Citrate | 2.32 | — | 2.0 | 2.0 | 2.0 |
| Zinc Chloride | 0.05 | 0.01 | 0.05 | 0.1 | 0.5 |
| IPA | 2.0 | 2.0 | 2.0 | 2.0 | 2.0 |
| Propylene Glycol | 0.05 | 0.05 | 0.05 | 0.05 | 0.05 |
| Perfume | 0.1 | 0.1 | 0.1 | 0.1 | 0.1 |
| Total Surfactant | 0.9 | 0.9 | 0.9 | 0.9 | 0.9 |

Example 10 and 11

In Example 10, 1 wt % of a 1:1 LS-24-N to DTC surfactant mixture, 0.5 wt % fragrance, 5.0 wt % ethanol, and 0.5 wt % zinc chloride was added in that order to tap water while slowly stirring to form an effective deodorizing solution.

In Example 11, a solution was made similarly as in Example 10 but sodium citrate and citric acid was added to control the pH to be low 5.5.

Other variations and modifications of this invention will be apparent to those skilled in this art after careful study of this application. This invention is not to be limited except as set forth in the following claims.

What is claimed is:

1. A deodorizing composition consisting essentially of a clear, aqueous solution of divalent zinc ions in a deodorizing effective amount, and an anionic surfactant in an amount effective to solubilize said divalent zinc ions, such that said solution does not leave a visible residue on a substrate, wherein said anionic surfactant is described by the formula R—(O—CH$_2$—CH$_2$)$_x$—O—CH$_2$COO$^-$, wherein R is a fatty alcohol substituent or an alkylaryl substituent, the fatty alcohol substituent is a residue of a C$_6$–C$_{20}$ fatty alcohol, the alkylaryl substituent is a residue of a C$_{10}$–C$_{20}$ alkylaryl compound, and wherein X is at least 2.

2. The deodorizing composition according to claim 1, wherein X is from 2 to 20.

3. The deodorizing composition according to claim 1, wherein X is from 5 to 15.

4. The deodorizing composition according to claim 1, wherein said divalent zinc ions have a concentration of from about 0.01 wt % to about 5 wt % of the total aqueous solution.

5. The deodorizing composition according to claim 1, wherein said divalent zinc ions have a concentration of from about 0.02 wt % to about 2 wt % of the total aqueous solution.

6. The deodorizing composition according to claim 1, wherein said divalent zinc ions have a concentration of from about 0.03 wt % to about 0.3 wt % of the total aqueous solution.

7. The deodorizing composition according to claim 1, wherein said anionic surfactant has a concentration of from about 0.005 wt % to about 10 wt % of the total aqueous solution.

8. The deodorizing composition according to claim 1, wherein said anionic surfactant has a concentration of from about 0.2 wt % to about 1.0 wt % of the total aqueous solution.

9. The deodorizing composition to claim 1, wherein said anionic surfactant has a concentration of from about 0.50 wt % to about 0.75 wt % of the total aqueous solution.

10. The deodorizing composition according to claim 1, wherein said aqueous solution further includes a miscible cosolvent.

11. The deodorizing composition according to claim 10, wherein the miscible cosolvent is selected from the group consisting of ethanol, isopropanol, propylene glycol, and a glycol ether.

12. The deodorizing composition according to claim 10, wherein the miscible cosolvent is an ethylene oxide based glycol ether represented by the formula R—(OCH$_2$CH$_2$)$_x$OH, wherein R is selected from the group consisting of a methyl, ethyl, propyl, butyl and hexyl substituent, and x is 1 or 2.

13. The deodorizing composition according to claim 10, wherein the miscible cosolvent is a propylene oxide based glycol ether represented by the formula R—(OCH(CH$_3$)CH$_2$)$_x$OH, wherein R is selected from the group consisting of a methyl, ethyl, propyl, butyl and hexyl substituent, and x is 1 or 2.

14. The deodorizing composition according to claim 1, wherein said anionic surfactant is a carboxylate ion described by the formula R—(O—CH$_2$—CH$_2$)$_x$—O—CH$_2$COO$^-$, and wherein the carboxylate ion is formed from the associated salt of an ion selected from the group consisting of H$^+$, Na$^+$, K$^+$, NH$_4^+$, and mixtures thereof.

15. The deodorizing composition according to claim 1, wherein said aqueous solution has a pH from about 3 to about 8.

16. The deodorizing composition according to claim 1, wherein said aqueous solution has a pH from about 3 to about 7.

17. The deodorizing composition according to claim 1, wherein said aqueous solution has a pH from about 3 to about 6.

18. A method to deodorize a substrate comprising the step of applying a clear, aqueous solution to the substrate that does not leave a visible residue thereon, wherein said aqueous solution consists essentially of divalent zinc ions in a deodorizing effective amount, and an anionic surfactant in an amount effective to solubilize said divalent zinc ions, wherein said anionic surfactant is described by the formula R—(O—CH$_2$—CH$_2$)$_x$—O—CH$_2$COO$^-$, wherein R is a fatty alcohol substituent or an alkylaryl substituent, the fatty alcohol substituent is a residue of a C$_6$–C$_{20}$ fatty alcohol, the alkylaryl substituent is a residue of a C$_{10}$–C$_{20}$ alkylaryl compound, and wherein X is at least 2.

* * * * *